United States Patent
Vasily et al.

(10) Patent No.: US 6,514,242 B1
(45) Date of Patent: Feb. 4, 2003

(54) METHOD AND APPARATUS FOR LASER REMOVAL OF HAIR

(76) Inventors: David Vasily, 2114 Sycamore St., Bethlehem, PA (US) 18017; Peter Ladislaus Dorogi, 5 Sawmill Rd., Norwalk, CT (US) 06851

( * ) Notice: Subject to any disclaimer, the term of this patent is extended or adjusted under 35 U.S.C. 154(b) by 0 days.

(21) Appl. No.: 09/394,171

(22) Filed: Sep. 13, 1999

Related U.S. Application Data

(60) Provisional application No. 60/110,732, filed on Dec. 3, 1998.

(51) Int. Cl.[7] .............................................. A61B 18/18
(52) U.S. Cl. ................................ 606/9; 606/3; 606/10; 128/898; 600/306; 600/310; 607/88; 607/89
(58) Field of Search ......................... 606/3, 9, 13, 127, 606/128, 10; 128/898; 607/88, 89; 600/306, 310

(56) References Cited

U.S. PATENT DOCUMENTS

| | | | | | |
|---|---|---|---|---|---|
| 5,671,735 | A | * | 9/1997 | MacFarlane et al. | 128/633 |
| 6,015,404 | A | * | 1/2000 | Altshuler et al. | 606/9 |
| 6,050,990 | A | * | 4/2000 | Tankovich et al. | 606/9 |
| 6,149,644 | A | * | 11/2000 | Xie | 606/9 |
| 6,168,589 | B1 | * | 1/2001 | Tobnick | 606/9 |
| 6,168,590 | B1 | * | 2/2001 | Neev | 606/9 |
| 6,251,100 | B1 | * | 6/2001 | Flock et al. | 606/2 |
| 6,308,088 | B1 | * | 10/2001 | MacFarlane et al. | 600/310 |

OTHER PUBLICATIONS

*RRA Papers 052897–WP–5K, Hair Removal Using Light*, by R. Rox Anderson, MD, Harvard University, Massachusetts General Hospital—Mar., 1997.

*RRA Papers 052897–WP–5K, Safety And Efficacy of the Palomar Ruby Laser For Hair Removal*, by R. Rox Anderson, MD, Harvard Medical School—Mar., 1997.

* cited by examiner

*Primary Examiner*—Linda C. M. Dvorak
*Assistant Examiner*—Ahmed M Farah
(74) *Attorney, Agent, or Firm*—Charles A. Wilkinson; Clinton H. Wilkinson

(57) ABSTRACT

A method for removing hairs from living skin is provided which includes steps of measuring with a colorimeter the color of the area of the skin where the hair is to be removed to obtain a color value, employing the color value to select an optimum range of laser energy necessary to kill hair follicles in the area yet minimize inflammatory reaction, and directing the laser energy of the optimum range at the skin area.

18 Claims, No Drawings

METHOD AND APPARATUS FOR LASER REMOVAL OF HAIR

This application claims the benefit of provisional application No. 60/110,732 filed on Dec. 3, 1998.

BACKGROUND OF THE INVENTION

1. Field of the Invention

The invention concerns a method and apparatus for removing hair from living skin while minimizing irritation to the skin.

2. The Related Art

Location, location, location. Just like in real estate, the beauty of hair is where it rises. A forest of hair on the scalp is a blessing. On the upper lip it may be less desirous, most especially less desirous for females. Location on the legs is deemed also not attractive.

Removal of unwanted hair is commonly achieved by shaving for short term results. Mechanical epilation with wax or other devices provides a longer respite. Several disadvantages accompany these methods. Frequently they cause irritation, folliculitis and on rare occasions scarring. There are presently two FDA-approved treatments for hair removal. Electrolysis involves resistive heating around an electrode placed deeply into a hair follicle, causing complete or partial destruction. The treatment is painful, tedious and only moderately effective. About 50 to 85% of treated hairs regrow. There are also significant risk effects here of folliculitis and infection.

Another FDA-cleared treatment (Thermolase technique) involves exposure to a Q-switched Nd:YAG laser designed for tattoo removal, following wax epilation and topical application of a suspension of amorphous carbon particles. This treatment is mildly painful. Despite aggressive marketing, its effectiveness appears to be minimal or nonexistent. The potential complications of this treatment are those of laser surgery in general (infection, scarring, pigmentary changes), plus the risk of inadvertent tattooing by introducing carbon into the dermis through ruptured follicles. However, these complications presumably occur at an acceptably low incidence.

A safer and more effective system has been described by Dr. Rox Anderson of the Harvard Medical School and commercialized by Palomar Corporation. The system uses a ruby laser with light delivered through a transparent actively-cool sapphire hand piece held directly in contact with the skin. The hand piece conducts heat away from the epidermis before, during and after each pulse.

Transient inflammatory reaction (erythema, edema) and pigmentary changes (hypopigmentation, hyperpigmentation) are routine and expected whenever a laser is used to injure some component of the skin. Compared with pulsed dye, Q-switched and other lasers used for cosmetic procedures, the Palomar laser produces similar skin injury followed by rapid healing requiring minimal wound care. Compared with electrolysis, in which bacteria are repeatedly introduced into follicles from the skin surface by a needle-like electrode, the Palomar system may cause less folliculitis. Nonetheless, it is very evident there is a need for much safer procedures to avoid skin damage and to also minimize the number of treatments required for effective removal.

Accordingly, it is an object of the present invention to provide a method for epilation which minimizes transient inflammatory reactions and pigmentary changes.

Another object of the present invention is to provide an epilation method based on laser energy which minimizes the number of treatments necessary to effect full epilation.

These and other objects of the present invention become more apparent from the following summary and detailed description.

SUMMARY OF THE INVENTION

A method is provided for removing hair from body skin which includes:

(i) measuring with a colorimeter color of an area of the skin where hair is to be removed to obtain a color value;

(ii) employing the color value to determine an optimum range of laser energy necessary to kill hair follicles in the area yet minimizing inflammatory reactions; and (iii) directing laser energy of the optimum range at the skin area.

A kit is also provided for removing hair from body skin which includes a laser and instructions for operating the laser to remove the hair from the body skin.

DETAILED DESCRIPTION OF THE INVENTION

Now it has been discovered that laser-based removal of hair can be rendered more effective while less irritating through guidance by skin coloration type in selecting the most efficient laser energy dosage. Colorimetry values obtained from a spectrophotometer can now guide selection of the optimal laser energy.

According to a first step of the method of this invention, skin color is analyzed by a spectrophotometer/colorimeter. These instruments usually operate with at least one visible light source such as a light emitting diode (LED), xenon-arc, tungsten/halogen or other light source in the wavelength range of 400 to 900 nm. The visible light source may be co-housed with the sensor portion of the spectrophotometer/colorimeter. Both visible and infrared wavelength light may be utilized in connection with a sensor portion. A suitable hand-held instrument is commercially available from Minolta Camera Company Ltd., Japan (Minolta Spectrophotometer/Colorimeter CM-2002), from Colortec Associates, Accuracy Measurements Inc. and X-Rite.

Skin coloration can be expressed in values of lightness, redness and yellowness respectively denoted by $L^*$, $a^*$ and $b^*$ units.

The $L^*a^*b^*$ color space is related to the Individual Typology Angle, which is essentially the value of 57.3 arctangent $[(L^*-50)/b^*]$, identifying skin types. See Chardon et al., International Journal of Cosmetic Science, 13, 191–208 (1991). Type I, the very lightest skin color, covers an angle ranging from more than 55 to 60°; Type II, light skin color, covers an angle ranging from more than 41 to 55°; Type III, intermediate skin color, covers an angle ranging from more than 28 to 41°; Type IV, tan skin color, covers an angle ranging from more than 10 to 28°; and Type V, brown skin color, covers an angle ranging from 0 to 10°.

Individual Typology Angle correlates to a first approximation with visibly judged Skin Type and to a first approximation determines the correct laser setting. However, visual judgement of Skin Type may also be influenced by optical contributions from hemoglobin as well as that of melanin. A second shortcoming of the currently practiced art of Skin Typing is the phenomenon called metamerism, in which two skin colors that appear the same to the human eye under one light source are seen to be different under other lighting conditions. Human skin is metameric because people of different ethnic origins can have different optical types of melanin in their skin. The colorimeter used in the present method is designed to provide L*a*b* values that are the best metameric fit (average) for fluorescent lighting, daylight and incandescent light. Since the ruby laser interacts selectively with melanin, the primary optical parameters to be chosen must be those most sensitive to skin melanin content for more accurate selections of laser dosage for epilation.

The melanin absorption of incident light has a lower amplitude for lighter skin and a greater amplitude for darker skin, respectively. In the former case the skin color spectrum is partly dominated by hemoglobin absorbance, in the latter case by melanin absorbance. For lighter skin (low melanin), the absorbance of primarily green light by hemoglobin imparts a reddish remittance to the skin. For darker skin (high melanin content), the strong absorbance of blue light imparts a green-red combination to the remittance, giving skin a brownish color. For Caucasian skin, Types I–III, a change in melanin has a greater impact on total blue remittance than on green remittance, where hemoglobin dominates. It would appear that the best indicator of differences in skin melanin content is an optical parameter that compares remittance intensities in the blue part of the spectrum (heavily reduced by melanin absorbance) against the green remittance (heavily reduced by hemoglobin absorbance). Consequently, for Skin Types I–IV, one can treat the green band remittance as a melanin-independent baseline against which differences in blue-band remittance indicate differences in skin melanin content.

The standard definition of color was set in 1931 with the definition of three types of standard remitted spectra, X,Y and Z. Approximately, X is a red remittance spectrum, Y is a green spectrum, and Z is a blue spectrum. The psychological color perception parameters L*a*b* are actually algebraic transformations of X,Y,Z that accommodate the human mind's relative sensitivities to the X-, Y- and Z-spectra:

$$L^* = 116(Y/Y_a)^{1/2} - 16$$

$$a^* = 500[(X/X_a)^{1/3} - (Y/Y_a)^{1/3}]$$

$$b^* = 200[(Y/Y_a)^{1/3} - (Z/Z_a)^{1/3}]$$

where $X_a$, $Y_a$, and $Z_a$ are maximum values of the remittance for the particular illumination intensity. Looking at these three definitions reveals that the quantity b* compares blue to green remittance, Z versus Y, which is the object of the present method.

Table I shows the range of Skin Types for sixty-seven panelists in a clinical study performed for the present invention. Data correlation between the measured angle and the Skin Type subjectively assigned in the study is weak, pointing out the inferiority of the known Skin Typing method.

TABLE I

| PATIENT | SKIN TYPE | (ARC TAN) ((L-50)/B))(57.3) |
|---|---|---|
| 1 | II | 33.44 |
| 2 | III | 36.19 |
| 3 | III | 44.41 |
| 4 | II | 52.12 |
| 5 | I | 41.92 |
| 6 | II | 32.35 |
| 7 | III | 45.00 |
| 8 | II | 54.29 |

TABLE I-continued

| PATIENT | SKIN TYPE | (ARC TAN) ((L-50)/B))(57.3) |
|---|---|---|
| 9 | III | 43.78 |
| 10 | III | 55.25 |
| 11 | II | 35.51 |
| 12 | II | 37.37 |
| 13 | II | 40.68 |
| 14 | II | 44.63 |
| 15 | IV | 20.24 |
| 16 | II | 50.37 |
| 17 | III | 33.85 |
| 18 | III | 28.79 |
| 19 | II | 50.07 |
| 20 | II | 23.92 |
| 21 | III | 58.20 |
| 22 | III | 22.85 |
| 23 | II | 34.80 |
| 24 | III | 37.54 |
| 25 | III | 48.45 |
| 26 | III | 51.51 |
| 27 | III | 43.15 |
| 28 | III | 60.96 |
| 29 | II | 48.57 |
| 30 | II | 41.13 |
| 31 | III | 33.38 |
| 32 | III | 41.36 |
| 33 | III | 24.25 |
| 34 | I | 38.63 |
| 35 | IV | 29.06 |
| 36 | I | 52.86 |
| 37 | I | 58.44 |
| 38 | II | 47.78 |
| 39 | III | 35.86 |
| 40 | I | 53.92 |
| 41 | III | 22.80 |
| 42 | V | 6.98 |
| 43 | IV | 31.88 |
| 44 | II | 36.67 |
| 45 | II | 48.48 |
| 46 | I | 59.56 |
| 47 | II | 54.52 |
| 48 | III | 49.43 |
| 49 | I | 60.54 |
| 50 | II | 52.97 |
| 51 | II | 51.50 |
| 52 | II | 51.63 |
| 53 | II | 52.14 |
| 54 | II | 31.94 |
| 55 | II | 51.17 |
| 56 | IV | 38.13 |
| 57 | — | 37.91 |
| 58 | IV | 35.60 |
| 59 | II | 46.49 |
| 60 | III | 49.52 |
| 61 | — | 48.53 |
| 62 | III | 31.05 |
| 63 | III | 25.52 |
| 64 | III | 44.20 |
| 65 | III | 41.45 |
| 66 | II | 63.19 |
| 67 | II | 33.58 |

TABLE II

| | L*a*b* (Laser Dose J/cm²) | | | | |
|---|---|---|---|---|---|
| PATIENT | SKIN TYPE | L* | a* | b* | LASER DOSE (J/cm²) |
| 1 | II | 60.26 | 11.94 | 15.54 | 18 |
| 2 | III | 60.74 | 14.72 | 14.68 | 21 |
| 3 | III | 65.40 | 6.10 | 15.72 | 18 |
| 4 | II | 66.84 | 6.68 | 13.10 | 20 |
| 5 | I | 64.22 | 8.80 | 15.84 | 17 |
| 6 | II | 60.88 | 13.04 | 17.18 | 12 |

TABLE II-continued

L*a*b* (Laser Dose J/cm²)

| PATIENT | SKIN TYPE | L* | a* | b* | LASER DOSE (J/cm²) |
|---|---|---|---|---|---|
| 7 | III | 64.80 | 8.70 | 14.80 | 18 |
| 8 | II | 69.58 | 5.70 | 14.08 | 18 |
| 9 | III | 64.68 | 9.88 | 15.32 | 16 |
| 10 | III | 72.92 | 4.70 | 15.90 | 19 |
| 11 | II | 61.15 | 14.68 | 15.63 | 16 |
| 12 | II | 61.96 | 11.10 | 15.66 | 18 |
| 13 | II | 63.70 | 10.06 | 15.94 | 16 |
| 14 | II | 60.80 | 14.20 | 10.94 | 20 |
| 15 | IV | 56.68 | 11.54 | 18.12 | 10 |
| 16 | II | 66.66 | 10.64 | 13.80 | 18 |
| 17 | III | 61.28 | 12.04 | 16.82 | 15 |
| 18 | III | 59.22 | 11.06 | 16.78 | 12 |
| 19 | II | 67.05 | 7.05 | 14.28 | 18 |
| 20 | II | 56.82 | 17.42 | 15.38 | 12 |
| 21 | III | 70.06 | 4.80 | 12.44 | 18 |
| 22 | III | 56.86 | 13.78 | 16.28 | 12 |
| 23 | II | 61.16 | 12.66 | 16.06 | 18 |
| 24 | III | 62.60 | 14.90 | 16.40 | 18 |
| 25 | III | 67.60 | 8.05 | 15.60 | 18 |
| 26 | III | 67.10 | 8.35 | 13.60 | 18 |
| 27 | III | 64.23 | 10.63 | 15.18 | 18 |
| 28 | III | 71.67 | 4.23 | 12.03 | 20 |
| 29 | II | 64.66 | 9.34 | 12.94 | 18 |
| 30 | II | 62.40 | 12.50 | 14.20 | 25 |
| 31 | III | 61.30 | 11.20 | 17.15 | 18 |
| 32 | III | 64.42 | 7.70 | 16.38 | 14 |
| 33 | III | 57.62 | 14.10 | 16.92 | 12 |
| 34 | I | 62.00 | 11.30 | 15.02 | 20 |
| 35 | IV | 59.90 | 11.40 | 17.82 | 20 |
| 36 | I | 64.02 | 10.80 | 10.62 | 35 |
| 37 | I | 67.45 | 7.50 | 10.72 | 35 |
| 38 | II | 62.63 | 14.13 | 11.46 | 22 |
| 39 | III | 62.65 | 11.42 | 17.50 | 25 |
| 40 | I | 67.22 | 8.07 | 12.55 | 33 |
| 41 | III | 56.62 | 15.80 | 15.75 | 15 |
| 42 | V | 52.20 | 13.86 | 17.98 | 13 |
| 43 | IV | 61.32 | 11.92 | 18.20 | 21 |
| 44 | II | 60.70 | 13.65 | 14.37 | 20 |
| 45 | II | 65.47 | 12.47 | 13.70 | 25 |
| 46 | I | 66.42 | 10.65 | 9.65 | 25 |
| 47 | II | 67.70 | 9.23 | 12.62 | 30 |
| 48 | III | 65.80 | 9.65 | 13.53 | 20 |
| 49 | I | 70.00 | 7.07 | 11.30 | 30 |
| 50 | II | 66.30 | 9.90 | 12.30 | 25 |
| 51 | II | 67.60 | 7.40 | 14.00 | 25 |
| 52 | II | 66.90 | 9.86 | 13.38 | 30 |
| 53 | II | 66.80 | 7.87 | 13.06 | 30 |
| 54 | II | 60.26 | 13.20 | 16.46 | 22 |
| 55 | II | 68.96 | 8.80 | 15.26 | 30 |
| 56 | IV | 63.50 | 9.50 | 17.20 | 25 |
| 57 | — | 61.72 | 14.25 | 15.05 | 26 |
| 58 | IV | 61.67 | 13.12 | 16.30 | 15 |
| 59 | II | 62.85 | 11.95 | 12.20 | 35 |
| 60 | III | 65.85 | 9.85 | 13.53 | 20 |
| 61 | — | 68.80 | 5.82 | 16.62 | 30 |
| 62 | III | 58.97 | 16.12 | 14.90 | 22 |
| 63 | III | 57.70 | 16.06 | 16.13 | 25 |
| 64 | III | 63.37 | 14.40 | 13.75 | 20 |
| 65 | III | 63.00 | 12.58 | 14.72 | 20 |
| 66 | II | 69.15 | 4.57 | 9.68 | 25 |
| 67 | II | 57.90 | 17.45 | 11.90 | 20 |

TABLE III

| LASER DOSE (J/cm²) | b*/L | b* | a*/b* |
|---|---|---|---|
| 18 | 0.258 | 15.54 | 0.768 |
| 21 | 0.242 | 14.68 | 1.003 |
| 18 | 0.240 | 15.72 | 0.388 |
| 20 | 0.196 | 13.10 | 0.510 |
| 17 | 0.247 | 15.84 | 0.556 |
| 12 | 0.282 | 17.18 | 0.759 |
| 18 | 0.228 | 14.80 | 0.588 |
| 18 | 0.202 | 14.08 | 0.405 |
| 16 | 0.237 | 15.32 | 0.645 |
| 19 | 0.218 | 15.90 | 0.296 |
| 16 | 0.256 | 15.63 | 0.939 |
| 18 | 0.253 | 15.66 | 0.709 |
| 16 | 0.250 | 15.94 | 0.631 |
| 20 | 0.180 | 10.94 | 1.298 |
| 10 | 0.320 | 18.12 | 0.637 |
| 18 | 0.207 | 13.80 | 0.771 |
| 15 | 0.274 | 16.82 | 0.716 |
| 12 | 0.283 | 16.78 | 0.659 |
| 18 | 0.213 | 14.28 | 0.494 |
| 12 | 0.271 | 15.38 | 1.133 |
| 18 | 0.178 | 12.44 | 0.386 |
| 12 | 0.286 | 16.28 | 0.846 |
| 18 | 0.263 | 16.06 | 0.788 |
| 18 | 0.262 | 16.40 | 0.909 |
| 18 | 0.231 | 15.60 | 0.516 |
| 18 | 0.203 | 13.60 | 0.614 |
| 18 | 0.236 | 15.18 | 0.700 |
| 20 | 0.168 | 12.03 | 0.352 |
| 18 | 0.200 | 12.94 | 0.722 |
| 25 | 0.228 | 14.20 | 0.880 |
| 18 | 0.280 | 17.15 | 0.653 |
| 14 | 0.254 | 16.38 | 0.470 |
| 12 | 0.294 | 16.92 | 0.833 |
| 20 | 0.242 | 15.02 | 0.752 |
| 20 | 0.297 | 17.82 | 0.640 |
| 35 | 0.166 | 10.62 | 1.017 |
| 35 | 0.159 | 10.72 | 0.700 |
| 22 | 0.183 | 11.46 | 1.233 |
| 25 | 0.279 | 17.50 | 0.653 |
| 33 | 0.187 | 12.55 | 0.643 |
| 15 | 0.278 | 15.75 | 1.003 |
| 13 | 0.344 | 17.98 | 0.771 |
| 21 | 0.297 | 18.20 | 0.655 |
| 20 | 0.237 | 14.37 | 0.950 |
| 25 | 0.209 | 13.70 | 0.910 |
| 25 | 0.145 | 9.65 | 1.104 |
| 30 | 0.186 | 12.62 | 0.731 |
| 20 | 0.206 | 13.53 | 0.713 |
| 30 | 0.161 | 11.30 | 0.626 |
| 25 | 0.186 | 12.30 | 0.805 |
| 25 | 0.207 | 14.00 | 0.529 |
| 30 | 0.200 | 13.38 | 0.737 |
| 30 | 0.196 | 13.06 | 0.603 |
| 22 | 0.273 | 16.46 | 0.802 |
| 30 | 0.221 | 15.26 | 0.577 |
| 25 | 0.271 | 17.20 | 0.552 |
| 26 | 0.244 | 15.05 | 0.947 |
| 15 | 0.264 | 16.30 | 0.805 |
| 35 | 0.194 | 12.20 | 0.980 |
| 20 | 0.205 | 13.53 | 0.728 |
| 30 | 0.242 | 16.62 | 0.350 |
| 22 | 0.253 | 14.90 | 1.082 |
| 25 | 0.280 | 16.13 | 0.996 |
| 20 | 0.217 | 13.75 | 1.047 |
| 20 | 0.234 | 14.72 | 0.855 |
| 25 | 0.140 | 9.68 | 0.472 |
| 20 | 0.206 | 11.90 | 1.466 |

A stronger determinant of the correct Laser Dose is the ratio of Z/Y, which is derivable from the ratio of b*/L*, as can be seen from the above-shown algebraic relations. Table II shows the range of colorimetric values for skin sites from 67 individuals. Table III shows the range of values for Laser Dose versus b*, b*/L* and (for an arbitrary comparison) a*/b*. There is a strong linear correlation between laser dose and b* or b*/L* which can be seen when the values are graphed. In contrast, a*/b*, which is dominated by the X coordinate rather than the interrelationship of Z and Y, has a very poor correlation with Laser Dose.

Based on the calculation of statistical correlation coefficients ($R^2$), the strongest correlation with the correct Laser Dose was found for $b^*/L^*$. A linear fit to the data gives the mathematical expression for the Fluence (Laser Dose) in joules/cm$^2$ as $$\text{Laser Dose} = 39 - 84(b^*/L^*)$$

The correlations L* versus Laser Dose and a* versus Laser Dose were found to be weaker. This is expected since both L* and a* are independent of Z and hence less sensitive to melanin.

Changes in the type of laser employed, cooling head configuration applied at the interface between skin and laser energy and temperature, as well as other physical factors may lead to different constants. Therefore the Laser Dose is best described by an overall general equation of the following type:

$$\text{Laser Dose} = k^1 - k^2(b^*/L^*)$$

where $k^1$ ranges from 1 to 60, preferably from 25 to 50, optimally from 30 to 40; and $k^2$ ranges from 1 to 120, preferably from 10 to 110, more preferably from 50 to 100, optimally from 55 to 85.

Any of the concepts and theories as well as the mathematical correlation of this invention should not be considered as limiting the actual invention itself. Adjustments to the theory may be deemed appropriate in the future but this will not negate the underlying discovery of using specific calorimetric parameters to determine the optimum laser energy dosage added for hair removal.

For purposes of this invention, most preferred is a ruby laser with output wavelength of 694 nm. Other types of lasers may also be employed. These include carbon dioxide based lasers and Q-switched Nd:YAG lasers pulsed at 1064 nm. Particularly useful may be an Alexandrite laser operating at 755 nm, a typical commercial instrument being the Gentle LASE available from the Candela Corporation, Wayland, Mass. A still further potentially useful laser is the KTP Crystal Diode type emitting at 810 nm, available from Coherent Corporation.

Advantageously, probes of lasers according to the present invention may include a cooling head. Temperatures ranging from 0° C. down to minus 80° C., preferably between 0° C. and minus 10° C. are employed for this invention. For instance, the Palomar Ruby Laser 2000 model operates at minus 10° C. utilizing a Thermatech Pump with a sapphire tip. A TFE cryogen sprayhead may also be employed and is commercially available with the Gentle Lase instrument from Candela Corporation.

Pulse duration is best when extended but only to the point falling short of skin damage. With the Palomar Ruby Laser (Epiwand instrument), there is a fixed duration of 3 milliseconds for each pulse. Generally pulse duration may range from about 0.5 to about 10 milliseconds.

A first embodiment of equipment for purposes of this invention includes a spectrophotometer/colorimeter physically separate from the laser. Information gathered from L*a*b* measurement or color matching of skin type is utilized to adjust laser dose levels. Input to the laser on dosage may either be through manual adjustment or automatic by electronic transfer. Skin color values can be sent to a computer program which then automatically sets energy dosage in the laser. A second embodiment of equipment for purposes of this invention combines in a single instrument the spectrophotometer/colorimeter and laser. Circuitry and a logic chip allows color value to be measured and dosage level set in a seamless, fully automatic mode.

Except in the operating and comparative examples, or where otherwise explicitly indicated, all numbers in this description indicating amounts of material ought to be understood as modified by the word "about".

The foregoing description illustrates selected embodiments of the present invention. In light thereof variations and modifications will be suggested to one skilled in the art, all of which are within the spirit and purview and this invention.

What is claimed is:

1. A method for removing hair from body skin comprising:
   (i) measuring with a colorimeter color of an area of the skin where hair is to be removed to obtain a numerical color value expressing the relative green and blue remittance of said skin in a previously validated form related to a therapeutic dosage of laser light which will inactivate hair follicles without permanent harm to surrounding tissues;
   (ii) employing the color value to determine an optimum numerical range of laser energy necessary to inactivate hair follicles in the area yet minimize inflammatory reactions; and
   (iii) directing laser energy of the optimum range at the skin area.

2. The method according to claim 1 wherein the color value is defined by the L*a*b* system of color coordinates.

3. The method according to claim 2 wherein the laser energy is provided in a dose following the formula:

$$\text{Laser Dose} = k^1 - k^2(b^*/L^*)$$

wherein $k^1$ ranges from 1 to 60 and $k^2$ ranges from 1 to 120.

4. The method according to claim 3 wherein the laser energy is delivered by a ruby laser.

5. The method according to claim 4 wherein the ruby laser operates at 694 nm.

6. The method according to claim 3 wherein laser energy is delivered with a 3 millisecond pulse.

7. The method according to claim 3 wherein the skin is of a human body in areas selected from the group consisting of face, scalp, hands and legs.

8. The method according to claim 6 wherein the area is between the nose and lips.

9. A kit for removing hair from body skin comprising:
   (a) a laser; and
   (b) a colorimeter
   (c) instructions for operating the laser to remove hair from body skin, the instructions comprising:
      (i) measuring with the colorimeter color of an area of the skin where hair is to be removed to obtain a color value expressing the relative green and blue remittance of said skin in a previously validated form related to a therapeutic dosage of laser light which will inactivate hair follicles without permanent harm of surrounding tissues;
      (ii) employing the color value to determine an optimum range of laser energy necessary to kill hair follicles in the area yet minimizing inflammatory reactions; and
      (iii) directing laser energy of the optimum range at the skin area.

10. The kit according to claim 9 wherein the color value is defined by the L*a*b* system of color coordinates.

11. The kit according to claim 10 wherein the laser energy is provided in a dose according to the equation:

$$\text{Laser Dose} = k^1 - k^2(b^*/L^*)$$

wherein $k^1$ ranges from 1 to 60 and $k^2$ ranges from 1 to 120.

12. The kit according to claim 11 wherein the laser energy is delivered by a ruby laser.

13. The kit according to claim 12 wherein the ruby laser operates at 694 nm.

14. The kit according to claim 9 wherein the laser energy is delivered from the laser with a 3 millisecond pulse.

15. A method for removing hair from body skin comprising:
    (a) measuring with a colorimeter color of an area of the skin where hair is to be removed to obtain a color value;
    (b) employing the color value to determine an optimum range of laser energy necessary to kill hair follicles in the area yet minimizing inflammatory reactions; and
    (c) directing laser energy of the optimum range at the skin area, and
    (d) wherein the color value is defined by the L*a*b* System of color coordinates.

16. The method according to claim 15 wherein the laser energy is provided in a dose following the formula:

$$\text{Laser Dose} = k^1 - k^2(b^*/L^*)$$

wherein $k^1$ ranges from 1 to 60 and $k^2$ ranges from 1 to 120.

17. A kit for removing hair from body skin comprising:
    (a) a laser; and
    (b) instructions for operating the laser to remove hair from body skin, the instructions comprising:
        (i) measuring with a colorimeter color of an area of the skin where hair is to be removed to obtain a color value;
        (ii) employing the color value to determine an optimum range of laser energy necessary to kill hair follicles in the area yet minimizing inflammatory reactions; and
        (iii) directing laser energy of the optimum range at the skin area, and
        (iv) wherein the color value is defined by the L*a*b* System of color coordinates.

18. A kit for removing hair from body skin according to claim 17 wherein the laser energy is provided in a dose following the formula:

$$\text{Laser Dose} = k^1 - k^2(b^*/L^*)$$

wherein $k^1$ ranges from 1 to 60 and $k^2$ ranges from 1 to 120.

* * * * *